US011260180B2

(12) United States Patent
Ra

(10) Patent No.: US 11,260,180 B2
(45) Date of Patent: Mar. 1, 2022

(54) SYRINGE

(71) Applicant: Yong-Kuk Ra, Gumi-si (KR)

(72) Inventor: Yong-Kuk Ra, Gumi-si (KR)

( * ) Notice: Subject to any disclaimer, the term of this patent is extended or adjusted under 35 U.S.C. 154(b) by 237 days.

(21) Appl. No.: 16/068,962

(22) PCT Filed: Jan. 13, 2017

(86) PCT No.: PCT/KR2017/000435
§ 371 (c)(1),
(2) Date: Jul. 10, 2018

(87) PCT Pub. No.: WO2017/131370
PCT Pub. Date: Aug. 3, 2017

(65) Prior Publication Data
US 2019/0009031 A1 Jan. 10, 2019

(30) Foreign Application Priority Data

Jan. 27, 2016 (KR) .................. 10-2016-0010355

(51) Int. Cl.
*A61M 5/31* (2006.01)
*A61M 5/32* (2006.01)
(Continued)

(52) U.S. Cl.
CPC ........ *A61M 5/3148* (2013.01); *A61M 5/3134* (2013.01); *A61M 5/3145* (2013.01);
(Continued)

(58) Field of Classification Search
CPC .......... A61M 5/3148; A61M 5/3134; A61M 5/3145; A61M 2005/3128; A61M 5/32;
(Continued)

(56) References Cited

U.S. PATENT DOCUMENTS

2008/0172006 A1* 7/2008 Hicks ................ A61M 39/24
    604/249
2010/0010450 A1* 1/2010 Runfola ............ A61M 5/3234
    604/190

FOREIGN PATENT DOCUMENTS

JP      2005-143579     6/2005
KR   10-2013-0017575    2/2013
(Continued)

OTHER PUBLICATIONS

International Search Report for International Application No. PCT/KR2017/000435, dated Apr. 21, 2017.

*Primary Examiner* — Amber R Stiles
*Assistant Examiner* — Avery Smale
(74) *Attorney, Agent, or Firm* — LRK Patent Law Firm

(57) ABSTRACT

The present invention relates to a syringe, and more particularly, to an apparatus obtained by improving a conventional syringe formed with an injection flow passage including an injection needle, so as to share a portion of the injection flow passage except the injection needle or to form a suction flow passage completely independent of the injection flow passage, thereby further smoothing suction of a liquid medicine. The syringe is configured such that the separate suction flow passage bypassing the injection needle is formed in the conventional syringe to more smoothly perform suction of the liquid medicine, thereby maximizing user's convenience and marketability of the conventional syringe, and further configured to forcibly close the suction flow passage upon injection of the liquid medicine.

8 Claims, 8 Drawing Sheets

(51) Int. Cl.
*A61M 5/34* (2006.01)
*A61M 39/22* (2006.01)

(52) U.S. Cl.
CPC .............. *A61M 5/32* (2013.01); *A61M 5/346* (2013.01); *A61M 2005/3128* (2013.01); *A61M 2005/3142* (2013.01); *A61M 2005/3201* (2013.01); *A61M 2039/226* (2013.01); *A61M 2205/3334* (2013.01); *A61M 2205/3337* (2013.01)

(58) Field of Classification Search
CPC .......... A61M 5/346; A61M 2005/3142; A61M 2005/3201; A61M 2039/226; A61M 5/3293; A61M 5/3295; A61M 5/3297
See application file for complete search history.

(56) References Cited

FOREIGN PATENT DOCUMENTS

| | | | |
|---|---|---|---|
| KR | 10-2013-0049037 | 5/2013 | |
| KR | 20130049037 A * | 5/2013 | .......... A61M 5/1782 |
| KR | 10-2015-0018336 | 2/2015 | |
| KR | 10-1560149 | 10/2015 | |
| KR | 10-1563723 | 10/2015 | |

* cited by examiner

SYRINGE

CROSS-REFERENCE TO RELATED APPLICATIONS

The present application is a U.S. National Phase entry from International Application No. PCT/KR2017/000435, filed on Jan. 13, 2017, which claims priority to Korean Patent Application No. 10-2016-0010355, filed on Jan. 27, 2016, the disclosure of which is incorporated by reference herein in their entirety.

TECHNICAL FIELD

The present invention relates to a syringe, and more particularly, to an apparatus obtained by improving an conventional syringe formed with an injection flow passage including an injection needle, so as to share a portion of the injection flow passage except the injection needle or to form a suction flow passage completely independent of the injection flow passage, thereby further smoothing suction of a liquid medicine, wherein the apparatus is configured such that a separate suction flow passage bypassing the injection needle is formed in the conventional syringe to more smoothly perform the suction of the liquid medicine, thereby maximizing user's convenience and marketability of the product.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward.

In this conventional syringe, as the plunger 30 is retreated, a negative pressure is generated in the cylinder 20 and the cylinder is then filled with the injection liquid. As the plunger is moved forward, the injection liquid in the cylinder 20 is discharged through the injection needle by a positive pressure and then injected into a patient's body.

In use of this conventional syringe, however, if a diameter of the injection needle 10 is very small, the inside of the cylinder 20 is in a vacuum state due to the negative pressure but the suction of the liquid medicine is not performed smoothly even though a user retreats the plunger 30 in order to suck the liquid medicine.

This phenomenon tends to become severer when a filter for filtering out foreign substances such as glass fragments of an ampoule from liquid medicine is employed.

Accordingly, there are problems in that a large force or a long time is required to suck the liquid medicine, which is inconvenient to the user, and furthermore when the user releases the plunger 30 before the suction of the liquid medicine is completed, the plunger 30 is advanced by itself by the negative pressure generated in the cylinder 20 in a state where the liquid medicine is not sucked into the cylinder 20.

PRIOR ART DOCUMENT

Korean Patent Publication No. 10-1563723.

DISCLOSURE

Technical Problem

The present invention is conceived to solve these problems, and an object of the present invention is to provide a syringe configured such that a separate suction flow passage bypassing an injection needle is formed in a conventional syringe to more smoothly perform suction of a liquid medicine, thereby maximizing user's convenience and marketability of the product, and further configured to forcibly close the suction flow passage by a user's manipulation upon injection of the liquid medicine.

Technical Solution

The present invention is achieved by a syringe including an injection needle and a cylinder and formed with an injection flow passage extending from the cylinder to the injection needle, wherein the syringe further includes an opening/closing means for selectively opening or closing the injection flow passage; a suction flow passage formed from a pointed hollow cap to the cylinder and provided with a through-hole formed in any one of the injection needle, a connector for connecting the injection needle to the cylinder, and the cylinder to establish communication between an inside and an outside thereof; and a valve means for intermittently controlling opening or closing of the suction flow passage by a user's manipulation.

Here, the valve means may include a pin formed with a through-hole and inserted into a hub of the injection needle to a predetermined depth while traversing the suction flow passage, so that the valve means may maintain an open state of the suction flow passage when the through-hole is correspondingly aligned with the suction flow passage and may switch the suction flow passage to a closed state when an outwardly protruding end of the pin is pressed such that the through-hole is offset from the suction flow passage by a depth difference.

Similarly, the valve means may include a rotary pin formed with a through-hole and positioned to traverse the suction flow passage, so that the valve means may maintain an open state of the suction flow passage when the through-hole is correspondingly aligned with the suction flow passage and may switch the suction flow passage to a closed state when a rotary lever formed at an outwardly protruding end of the pin is rotated such that the through-hole is offset from the suction flow passage by a direction difference.

Alternatively, the valve means may include a hollow internal body formed with a through-hole and a pipe-shaped external body having an inner diameter corresponding to an outer diameter of the internal body, so that the valve means may maintain an open state of the suction flow passage in a state where the external body is spaced apart from the through-hole of the internal body, and may switch the suction flow passage to a closed state by causing an inner peripheral surface of the external body to close the through-hole formed in the internal body in response to a relative axial movement of the internal body and the external body.

In addition, the internal body and the external body may be configured to maintain the closed state of the suction flow passage by means of an interference fit between an outer peripheral surface of the internal body and the inner peripheral surface of the external body.

Similarly, the internal body and the external body may be configured to maintain the closed state of the suction flow passage by means of resilient coupling of unidirectionally inclined protrusions formed in the internal body and the external body, respectively.

Furthermore, it is most preferable that the internal body and the external body are configured to maintain the closed state of the suction flow passage by means of engagement of threads and formed in the internal body and the external body, respectively, in response to a rotation in one direction, and the suction flow passage is switchable to the open state again in response to a rotation in an opposite direction.

Preferably, the cap accommodates the opening/closing means and is formed with a part of the suction flow passage with a space between an outer periphery of the opening/closing means and an inner periphery of the cap; an adhesive material for fixing a needle body and a hub of the injection needle to each other is accommodated in the opening/closing means and thus isolated from the liquid medicine; and a filter for filtering foreign substances from the liquid medicine is further provided in the suction flow passage.

In addition, the opening/closing means is preferably interference-fitted into the hub or fastened to the hub by threads.

Moreover, it is preferable that the opening/closing means has an inclined surface formed on an inner peripheral surface thereof to guide entrance of the injection needle.

Advantageous Effects

The syringe of the present invention configured such that a separate suction flow passage bypassing an injection needle is formed in a conventional syringe performs more smooth suction of a liquid medicine, thereby maximizing user's convenience and marketability of the product, and forcibly closes the suction flow passage upon injection of the liquid medicine.

BEST MODE

Figure 1:
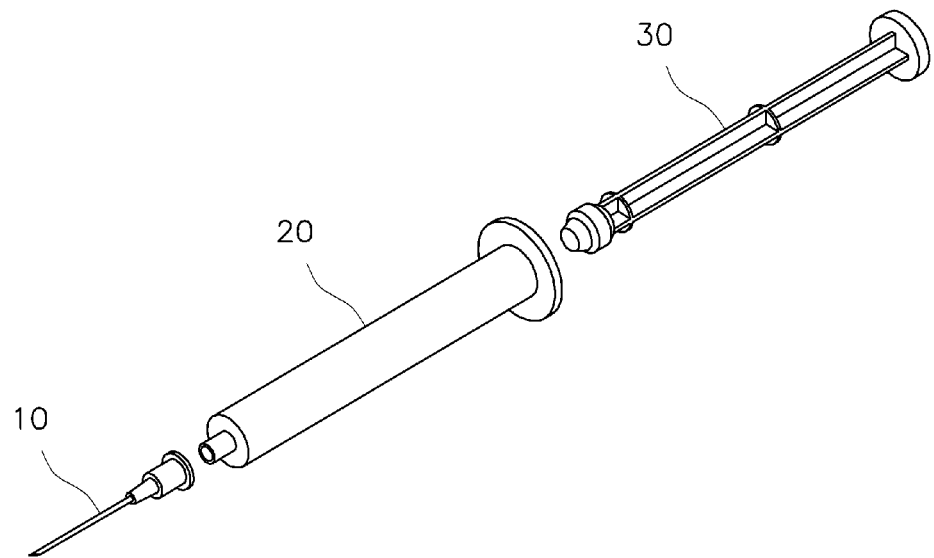
FIG. 1 is an exploded perspective view illustrating a conventional syringe.
Figure 2:
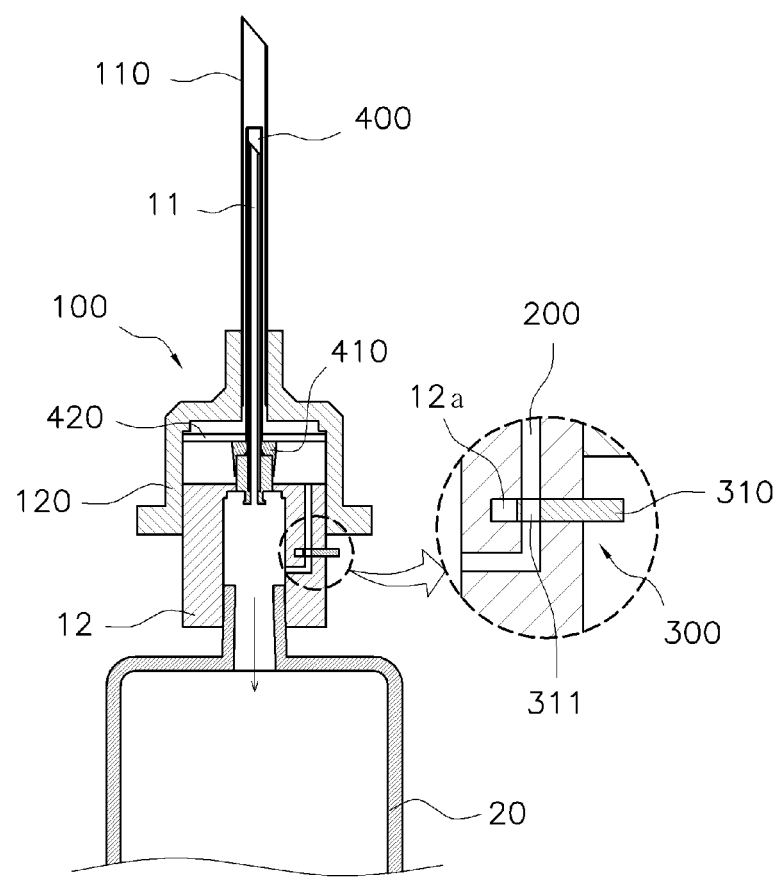
FIG. 2 is a sectional view illustrating a state where a valve means is opened in a first embodiment of a syringe according to the present invention.
Figure 3:
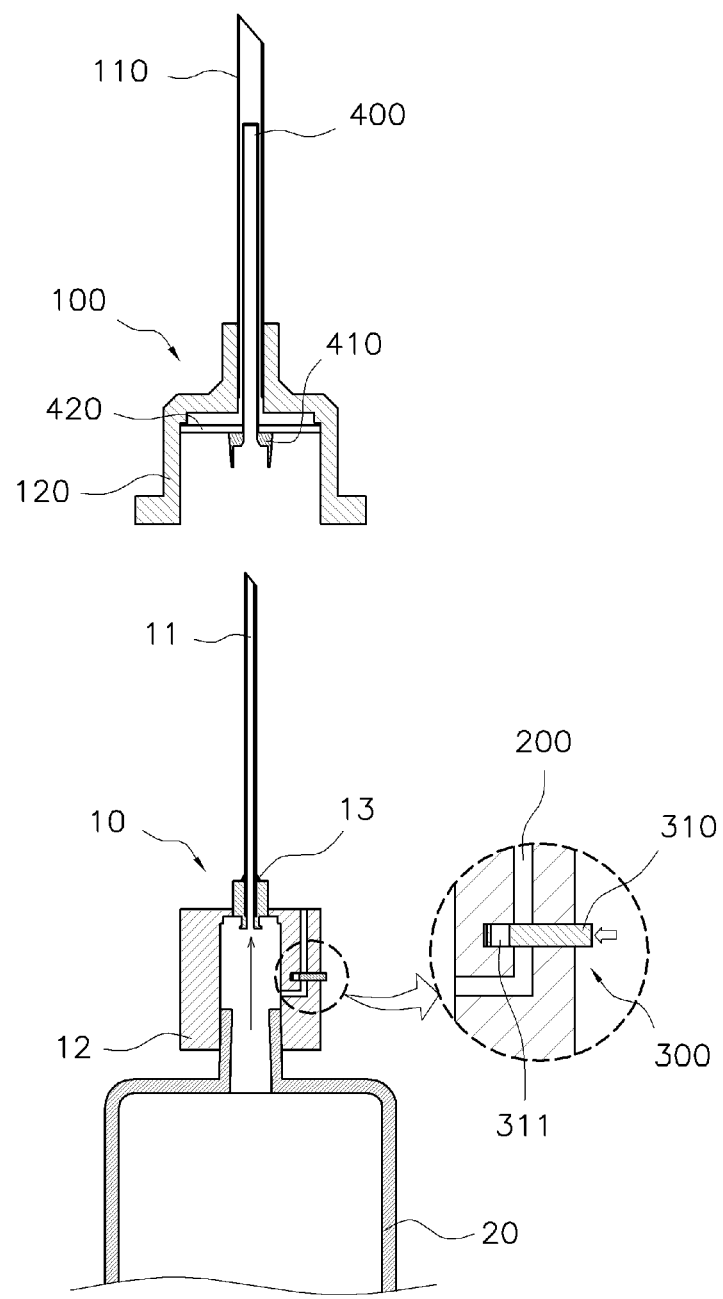
FIG. 3 is a sectional view illustrating a state where the valve means is closed in the first embodiment of the syringe according to the present invention.
Figure 4:
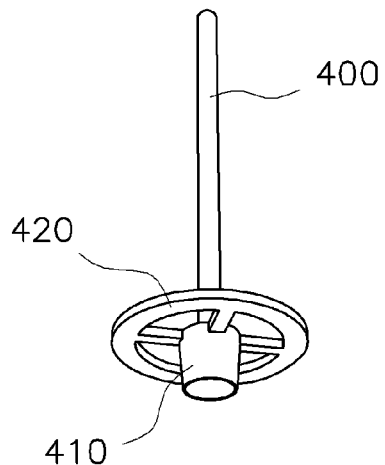
FIG. 4 is a perspective view illustrating an opening/closing means in the syringe according to the present invention.

FIG. 2 is a sectional view illustrating a state where a valve means is opened in a first embodiment of a syringe according to the present invention, FIG. 3 is a sectional view illustrating a state where the valve means is closed in the first embodiment of the syringe according to the present invention, and FIG. 4 is a perspective view illustrating an opening/closing means in the syringe according to the present invention.

Figure 5:
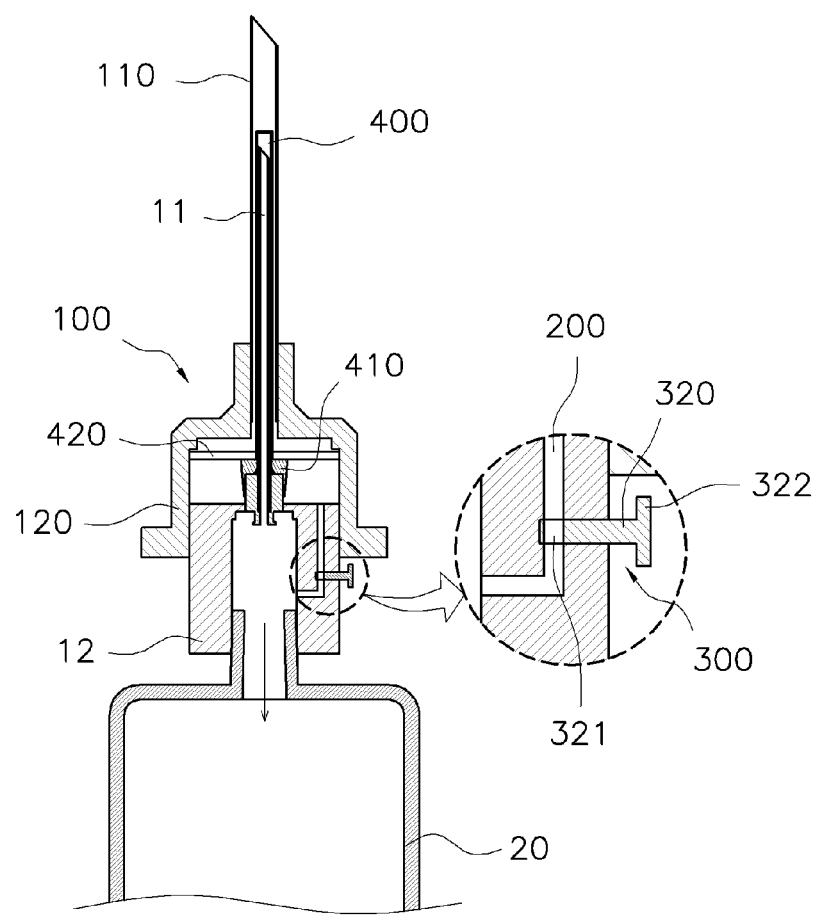
FIG. 5 is a sectional view illustrating a state where a valve means is opened in a second embodiment of the syringe according to the present invention.
Figure 6:
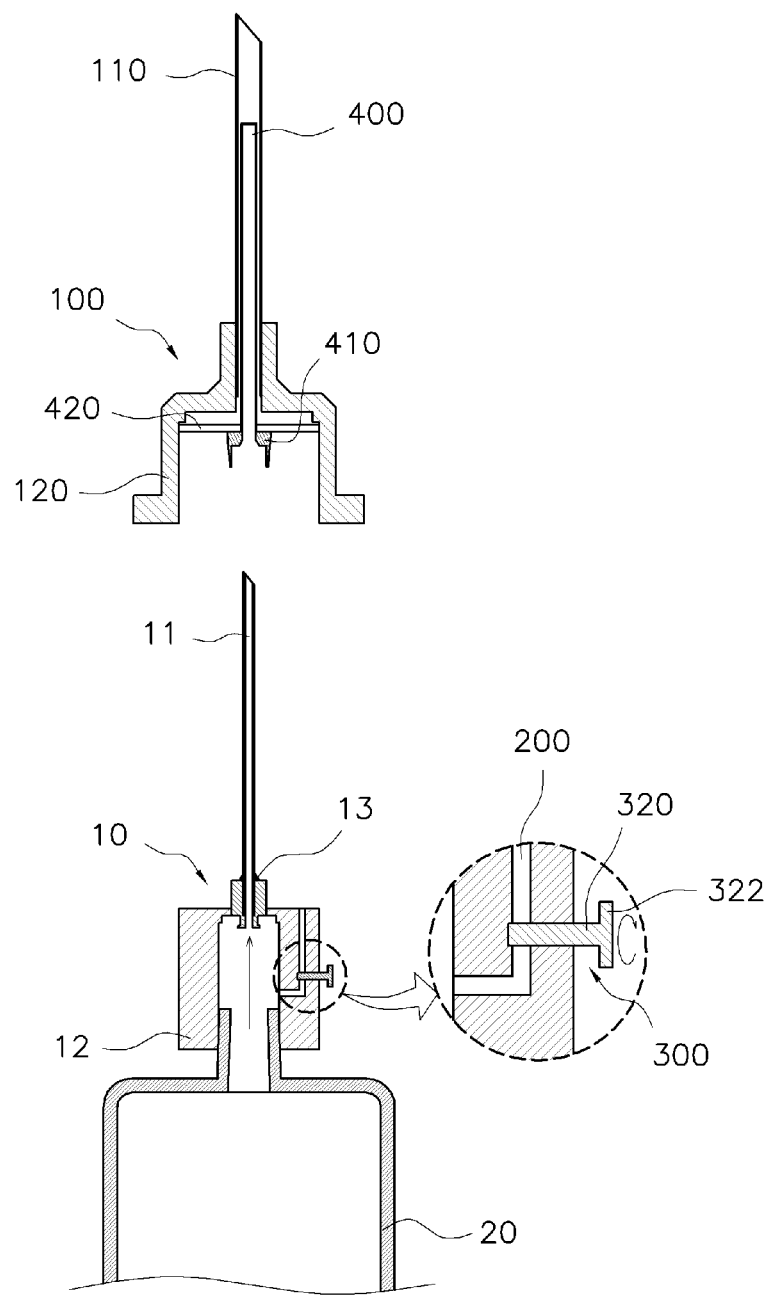
FIG. 6 is a sectional view illustrating a state where the valve means is closed in the second embodiment of the syringe according to the present invention.

Moreover, FIG. 5 is a sectional view illustrating a state where a valve means is opened in a second embodiment of the syringe according to the present invention, and FIG. 6 is a sectional view illustrating a state where the valve means is closed in the second embodiment of the syringe according to the present invention.

Figure 7:
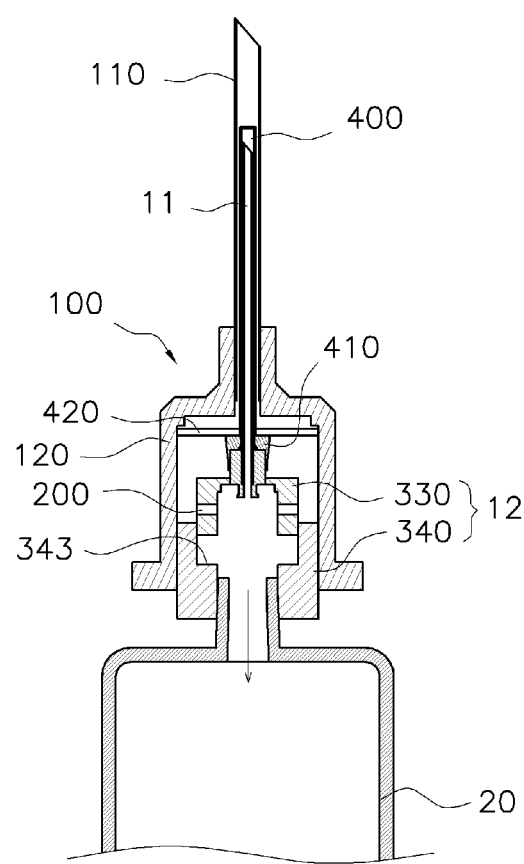
FIG. 7 is a sectional view illustrating a state where a liquid medicine is sucked in a third embodiment of the syringe according to the present invention.
Figure 8:
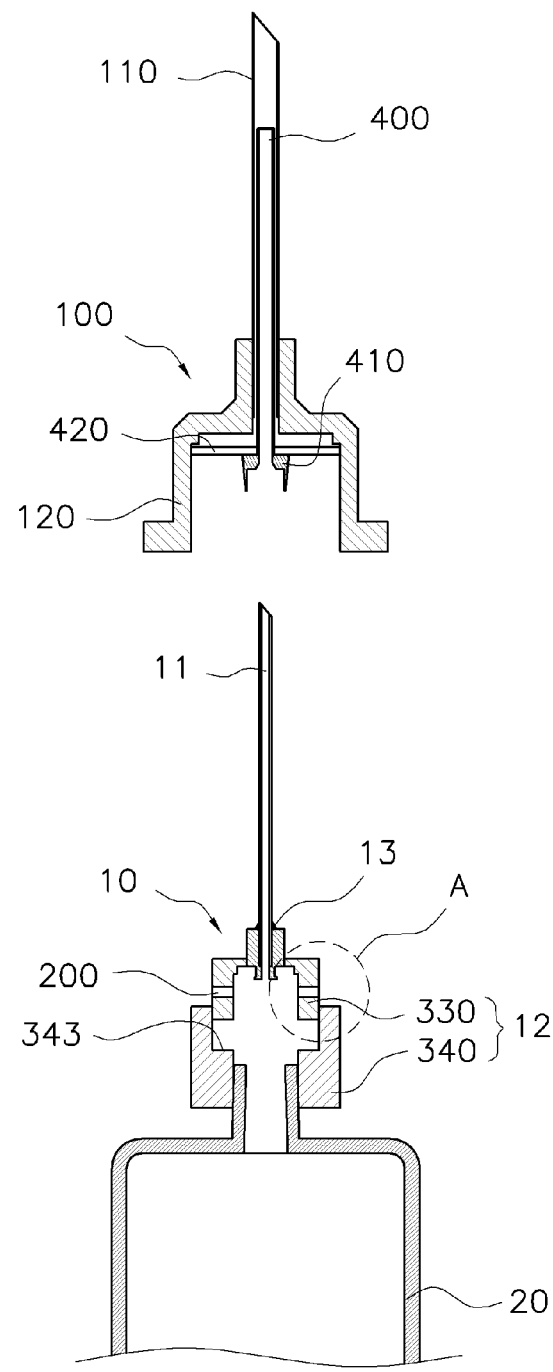
FIG. 8 is a sectional view illustrating a state where a cap is separated in the third embodiment of the syringe according to the present invention.
Figure 9:
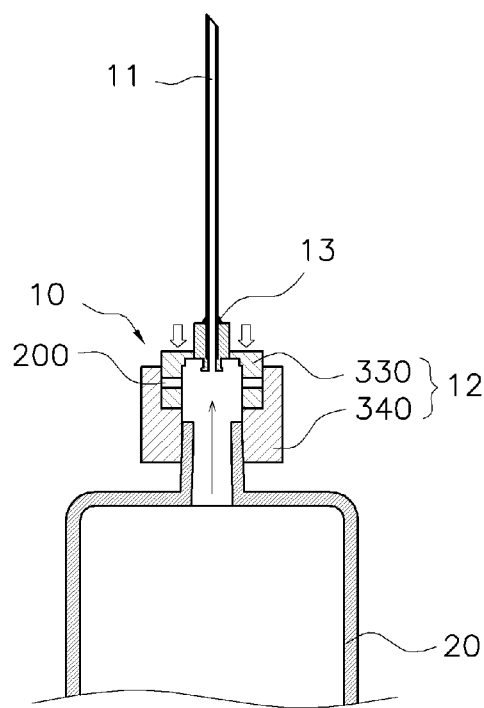
FIG. 9 is a sectional view illustrating a state where a valve means is closed in the third embodiment of the syringe according to the present invention.

Furthermore, FIG. 7 is a sectional view illustrating a state where a liquid medicine is sucked in a third embodiment of the syringe according to the present invention, FIG. 8 is a sectional view illustrating a state where a cap is separated in the third embodiment of the syringe according to the present invention, and FIG. 9 is a sectional view illustrating a state where a valve means is closed in the third embodiment of the syringe according to the present invention.

Figure 10:
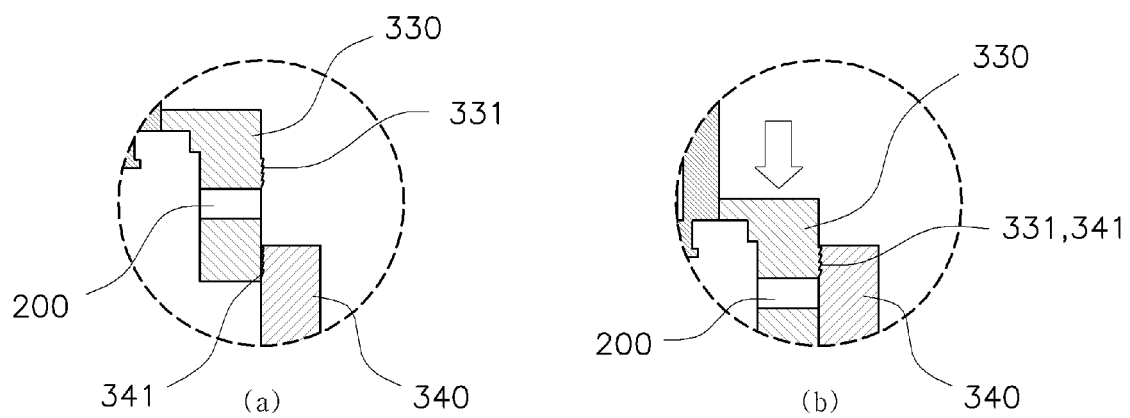
FIG. 10 is a sectional view illustrating a modified example of the third embodiment of the syringe according to the present invention.
Figure 11:
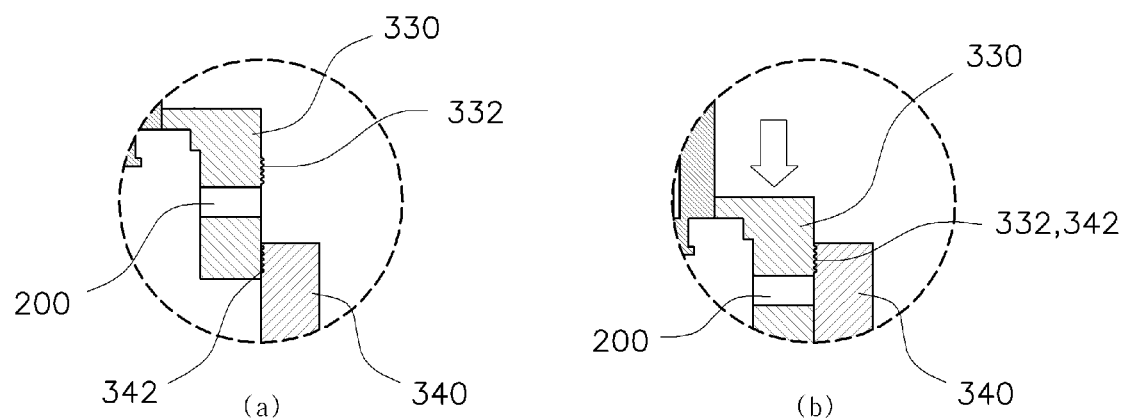
FIG. 11 is a sectional view illustrating main portions in a fourth embodiment of the syringe according to the present invention.
Figure 12:
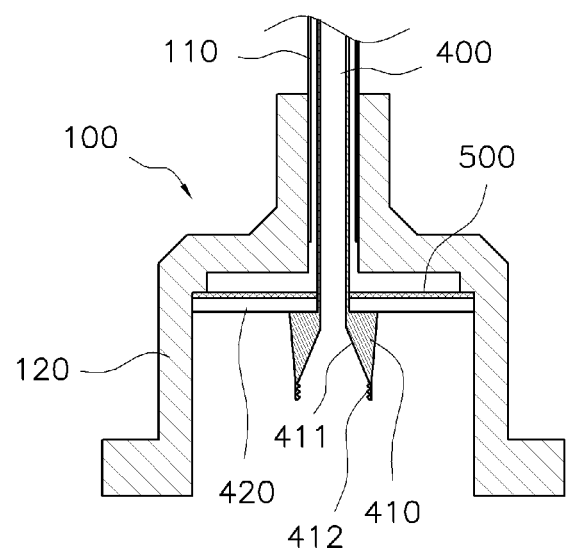
FIG. 12 is a view illustrating another example of the opening/closing means in the syringe according to the present invention.

Finally, FIG. 10 is a sectional view illustrating a modified example of the third embodiment of the syringe according to the present invention, FIG. 11 is a sectional view illustrating main portions in a fourth embodiment of the syringe according to the present invention, and FIG. 12 is a view illustrating another example of the opening/closing means in the syringe according to the present invention.

Embodiments of the present invention will be described below in detail with reference to the accompanying drawings.

As shown in FIGS. 2 to 12, a syringe according to the present invention is technically characterized in that a separate suction flow passage bypassing an injection needle is formed in a conventional syringe so as to perform smooth suction of a liquid medicine with a less force, thereby maximizing user's convenience and marketability of a product, and, in particular, enabling forcible closure of the suction flow passage upon injection of the liquid medicine.

The syringe of the present invention includes an injection needle 10 and a cylinder 20 and is formed with an injection flow passage extending from the cylinder 20 to the injection needle 10. The syringe further includes an opening/closing means 400 for selectively opening or closing the injection flow passage; a suction flow passage formed from a pointed hollow cap 100 to the cylinder 20 and provided with a through-hole 200 formed in any one of the injection needle 10, a connector for connecting the injection needle 10 to the cylinder 20 and the cylinder 20 to establish communication between an inside and an outside thereof; and a valve means 300 for intermittently controlling opening or closing of the suction flow passage by a user's manipulation.

That is, the present invention addresses an issue that a long time or a large force is required to suck the liquid medicine as the liquid medicine is sucked into the cylinder 20 only through the elongated injection needles 10, by additionally providing the opening/closing means 400 configured to temporarily close the injection needle 10 upon suction of the liquid medicine and by forming the suction flow passage capable of sucking the liquid medicine without passing through the injection needle 10 provided on the injection flow passage, whereby it is possible to easily and quickly perform the suction of the liquid medicine with a less force.

In addition thereto, the present invention more reliably closes the valve means 300, prevents the opening/closing means 400 from being unexpectedly separated from a hub 12, and enables the injection needle 10 to be more easily coupled to the opening/closing means 400.

To this end, in the present invention, the through-hole 200 provided on the suction flow passage is opened by the valve means 300 upon suction of the liquid medicine, and thus the liquid medicine is easily sucked into the cylinder 20 of the syringe without passing through the injection needle 10 and the opening/closing means 400 closes the injection needle 10 during this time.

On the contrary, upon injection of the liquid medicine, the through-hole 200 is closed by the valve means 300 to block the suction flow passage, while as the user removes the opening/closing means 400, the injection needle 10 is opened and the liquid medicine is then injected.

According to embodiments, the valve means 300 can be switched from an initial opened state to a closed state simply by a user's push or rotation manipulation.

In implementing the syringe of the present invention as described above, there may be the following four examples depending on whether the suction flow passage is an open type or a closed type and whether the user's manipulation for the valve means 300 is a push manipulation type or a rotation manipulation type. These examples will be separately described as the first to fourth embodiments, respectively.

First embodiment: Example in which for a closed type suction flow passage, the valve means 300 closes the suction flow passage by a user's push manipulation.

Second embodiment: Example in which for the closed type suction flow passage, the valve means 300 closes the suction flow passage by a user's rotation manipulation.

Third embodiment: Example in which for an open type suction flow passage, the valve means 300 closes the suction flow passage by a user's push manipulation.

Fourth embodiment: Example in which for the open type suction flow passage, the valve means 300 closes the suction flow passage by a user's rotation manipulation.

Here, the open type suction flow passage and the closed type suction flow passage will be described below.

First, the suction flow passage consists of a suction needle 110 of the cap 100→a cap hub 120 of the cap 100→the valve means 300→the hub 12 of the injection needle 10→the cylinder 20.

At this time, if the valve means 300 for the suction flow passage is positioned merely in an open space formed between an inner peripheral surface of the cap 100 and an outer peripheral surface of the hub 12, this suction flow passage will be referred to as the open type suction flow passage below, whereas if the valve means 300 for the suction flow passage is positioned in a closed tubular passage formed inside the cap hub 120 of the cap 100, this suction flow passage will be referred to as the closed type suction flow passage below.

Hereinafter, each of the embodiments will be described in greater detail.

(1) First Embodiment: Example in which for the Closed Type Suction Flow Passage, the Valve Means 300 Closes the Suction Flow Passage by a User's Push Manipulation In the first embodiment of the present invention, as illustrated in FIGS. 2 and 3, the valve means 300 includes a pin 310 formed with a through-hole 311 and inserted into the hub of the injection needle to a predetermined depth while traversing the suction flow passage, so that the valve means 300 may maintain an open state of the suction flow passage when the through-hole 311 is correspondingly aligned with the suction flow passage and may switch the suction flow passage to a closed state when an outwardly protruding end of the pin 310 is pressed such that the through-hole 311 is offset from the suction flow passage by a depth difference.

The cap 100 is to suck the liquid medicine from a liquid medicine-container, and includes the suction needle 110 and the cap hub 120. A tip of the suction needle 110 is inclined and pointed to penetrate a vial or the like, and is made of a metal material or a synthetic resin material so that it has a high strength.

In addition, the cap hub 120 is integrally coupled to and supports the suction needle 110, wherein an inner peripheral surface of the cap hub 120 is coupled to the outer peripheral surface of the hub 12 that supports a needle body 11 of the injection needle 10.

The needle body 11 and the hub 12 of the injection needle 10 are fixed to each other by an adhesive material 13 such as epoxy, wherein the hub 12 is hermetically assembled to the cylinder 20 of the syringe by a conventional interference fit.

In addition thereto, although the needle body 11 of the injection needle 10 is closed by the opening/closing means 400 upon suction of the liquid medicine, a user separates the opening/closing means 400 to open the needle body 11 upon injection of the liquid medicine.

In particular, in the present invention, the opening/closing means 400 may be configured to include a hermetic space 410 and a flange 420 as illustrated in FIG. 4.

In other words, the opening/closing means 400 has functions of closing the needle body 11 of the injection needle 10 upon suction of the liquid medicine and of opening the needle body 11 of the injection needle 10 upon injection of the liquid medicine. In the present invention, it is preferable that the opening/closing means 400 can be coupled to the hub 12 of the injection needle 10.

To this end, the hermetic space 410 is formed at a lower portion of the opening/closing means 400 so that the hermetic space 410 may surround and be coupled to the hub 12 of the injection needle 10.

In particular, in the present invention, it is preferable that the adhesive material 13 for securing the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

With this configuration, it is possible to prevent degradation of an adhesive force of the adhesive material 13 due to contact of the adhesive material 13 with the liquid medicine, or alteration of components of the liquid medicine caused by the adhesive material 13.

In addition thereto, the flange 420 provided in the opening/closing means 400 enables the opening/closing means 400 to be secured to the inner peripheral surface of the cap hub 120, if necessary.

FIG. 3 illustrates that the opening/closing means 400 is fixedly installed within the cap 100 so that the opening/closing means 400 is separated together with the cap 100 in response to separation of the cap 100, thereby opening the injection needle 10.

The through-hole 200 which is a closed type tubular passage is formed inside the hub 12 as a part of the suction flow passage, and the pin 310 is inserted into the hub 12 while traversing the through-hole 200.

It is preferable that this pin 310 has a polygonal cross-section to prevent rotation of the pin rather than a circular cross-section, and the pin 310 is formed with the through-hole 311 correspondingly aligned with the suction flow passage.

As a result, when the through-hole 311 of the pin 310 is positioned at the same depth as the suction flow passage, the suction flow passage is maintained in the open state.

In this regard, upon manufacture of the syringe of the present invention, the valve means is assembled such that the suction flow passage is in the open state as shown in FIG. 2.

However, when the user pushes the outward protruding end of the pin 310 so that the pin 310 is inserted into the hub 12, the through-hole 311 of the pin 310 is deeply positioned with respect to the suction flow passage as shown in FIG. 3, whereby the through-hole 311 is offset from the suction flow passage by such a depth difference so that the suction flow passage is switched to the closed state.

As a result, the valve means 300, which initially maintains the suction flow passage in the open state, may switch the suction flow passage to the closed state in response to the user's push manipulation.

To this end, the hub 12 is formed with a space 12*a* into which the pin 310 may be further inserted.

Accordingly, when the user separates the cap 100 and then pushes the pin 310 in order to inject the liquid medicine into the body, the injection flow passage consists of the cylinder 20→the hub 12 of the injection needle 10→the needle body 11 of the injection needle 10, as shown in FIG. 3.

At this time, the opening/closing means 400 is fixedly installed within the cap 100 to allow the opening/closing means 400 to be separated together with the cap 100 in response to the separation of the cap 100, thereby causing the injection needle 10 to be opened.

Accordingly, upon suction of the liquid medicine, the liquid medicine is sucked from the cap 100 into the cylinder through the valve means 300 which is in the open state, whereas upon injection of the liquid medicine, the liquid medicine is injected from the cylinder 20 through the opened injection needle 10.

As a result, it is possible to quickly suck and then rapidly discharge the liquid medicine, as required.

The syringe according to the present invention has an advantage that, when the liquid medicine is sucked into the syringe but is not immediately injected into the body, for example, even when a saline solution is sucked into the syringe and then injected into a liquid medicine container, which accommodates a powdered medicine, to dissolve the powdered medicine and a resulting mixture is sucked back into the syringe, the syringe can be conveniently used.

(2) Second Embodiment: Example in which for the Closed Type Suction Flow Passage, the Valve Means 300 Closes the Suction Flow Passage by a User's Rotation Manipulation In the second embodiment of the present invention, as illustrated in FIGS. 5 and 6, the valve means 300 includes a rotary pin 320 formed with a through-hole 321 and positioned to traverse the suction flow passage, so that the valve means 300 may maintain an open state of the suction flow passage when the through-hole 321 is correspondingly aligned with the suction flow passage and may switch the suction flow passage to a closed state when a rotary lever 322 formed at an outwardly protruding end of the pin 320 is rotated such that the through-hole 321 is offset from the suction flow passage by a direction difference.

In other words, the second embodiment of the present invention employs a known 2-way valve or a known 3-way valve.

In the second embodiment, descriptions of configurations which are common to those of the first embodiment will be omitted, and only configurations different from those of the first embodiment will be described below.

Even in the second embodiment, the through-hole 200 which is the closed type tubular passage is formed inside the hub 12 as a part of the suction flow passage, and the rotary pin 320 is inserted into the hub 12 to a predetermined depth while traversing the suction flow passage.

It is preferable that the rotary pin 320 has a circular cross-section so as to be rotatable about an axial center thereof and is formed with the through-hole 321 aligned in a direction corresponding to the suction flow passage.

In addition, the rotary lever 322 for rotating the rotatory pin 320 is formed at the protruding end of the rotary pin 320, so that the user may rotate the rotary pin 320 using the rotary lever 322.

As a result, when the through-hole 321 of the rotary pin 320 is aligned in the same direction as the suction flow passage, the suction flow passage is maintained in the open state as shown in FIG. 5.

However, when the user rotates the rotary pin 320 using the rotary lever 322, the through-hole 321 formed in the rotary pin 320 is positioned in a direction different from that of the suction flow passage, i.e., in a direction approximately perpendicular to the suction flow passage, whereby the suction flow passage is switched to the closed state as shown in FIG. 6 due to such a direction difference.

As a result, the valve means 300, which initially maintains the suction flow passage in the open state, can switch the suction flow passage to the closed state in response to the user's rotation manipulation.

Accordingly, when the user separates the cap 100 and then rotates the rotary pin 320 using the rotary lever 322 in order to inject the liquid medicine into the body, the injection flow passage consists of the cylinder 20→the hub 12 of the injection needle 10→the needle body 11 of the injection needle 10, as shown in FIG. 6.

Even at this time, the opening/closing means 400 is fixedly installed within the cap 100 to allow the opening/closing means 400 to be separated together with the cap 100 in response to the separation of the cap 100, thereby causing the injection needle 10 to be opened.

Accordingly, upon suction of the liquid medicine, the liquid medicine is sucked from the cap 100 into the cylinder through the valve means 300 which is in the open state, whereas upon injection of the liquid medicine, the liquid medicine is injected from the cylinder 20 through the opened injection needle 10.

As a result, it is possible to quickly suck and then rapidly discharge the liquid medicine, as required.

As compared with the first embodiment, the second embodiment has an advantage in that the valve means 300 may be closed and then be re-opened.

Next, the third embodiment and the fourth embodiment relate to the open type suction flow passage. The valve means 300 includes a hollow internal body 330 formed with the through-hole 200 and a pipe-shaped external body 340 having an inner diameter corresponding to an outer diameter of the internal body 330, so that the valve means 300 may maintain the open state of the suction flow passage in a state where the external body 340 is spaced apart from the through-hole 200 of the internal body 330, and may switch the suction flow passage to the closed state by causing an inner peripheral surface of the external body 340 to close the through-hole 200 formed in the internal body 330 in response to a relative axial movement of the internal body 330 and the external body 340.

(3) Third Embodiment: Example in which for the Open Type Suction Flow Passage, the Valve Means 300 Closes the Suction Flow Passage by a User's Push Manipulation In the third embodiment of the present invention, as illustrated in FIGS. 7 to 9, the internal body 330 and the external body 340 are configured such that the suction flow passage is maintained in the closed state by an interference fit between an outer peripheral surface of the internal body 330 and the inner peripheral surface of the external body 340.

In the third embodiment, descriptions of configurations which are common to those of the first or second embodiment will be omitted, and only configurations different from those of the first or second embodiment will be described below.

In the third embodiment, the open type suction flow passage as a part of the suction flow passage is formed between the inside of the cap 100 and the outside of the hub 12.

The hub 12 is divided into the internal body 330 and the external body 340, and a plurality of through-holes 200 are formed along a radial direction at the internal body 330.

The diameter and number of the through-holes 200 are determined to enable the liquid medicine to flow smoothly.

In addition, each of the internal body 330 and the external body 340 is formed of a hollow body so that the inner peripheral surface of the external body 340 may be slid over the external peripheral surface of the internal body 330.

As a result, the open state of the suction flow passage is maintained in a state where the external body 340 is spaced apart from the through-holes 200 of the internal body 330.

On the contrary, the inner peripheral surface of the external body 340 closes the through-holes 200 formed in the internal body 330 in response to the relative axial movement of the internal body 330 and the external body 340, thereby switching the suction flow passage to the closed state.

It is preferable that a shoulder 343 is formed on the external body 340 to define a lower limit level of the internal body 330.

In particular, in the third embodiment, the outer peripheral surface of the internal body 330 and the inner peripheral surface of the external body 340 are formed to be tapered at a predetermined angle, so that when the external body 340 closes the through-holes 200 of the internal body 330, both bodies may be coupled to each other by means of an interference fit.

As a modification of the aforementioned third embodiment, as shown in FIG. 10 which is an enlarged view of portion A in FIG. 8, it is preferable that the internal body 330 and the external body 340 are configured to maintain the closed state of the suction flow passage by means of resilient coupling of unidirectionally inclined protrusions 331 and 341 formed in the internal body 330 and the external body 340, respectively.

FIG. 10 (*a*) shows the open state of the through-holes 200 caused by the valve means 300, and FIG. 10 (*b*) shows the closed state of the through-holes 200 caused by the valve means 300.

In this modification of the third embodiment, the internal body 330 and the external body 340 are coupled to each other by the unidirectionally inclined protrusions 331 and 341, thereby reliably maintaining the state where the external body 340 closes the through-holes 200 of the internal body 330.

As a result, when the external body 340 is positioned to be spaced apart from the through-holes 200 of the internal body 330 as shown in FIG. 10 (*a*), the suction flow passage is maintained in the open state.

However, when the user separates the cap 100 and then simply pushes the internal body 330, the unidirectionally inclined protrusions 331 and 341 formed in the internal body 330 and the external body 340, respectively, resiliently ride over each other, and the external body 340 closes the through-holes 200 formed in the internal body 330 as shown in FIG. 10 (*b*), thereby switching the suction flow passage to the closed state.

As a result, the valve means 300, which initially maintains the suction flow passage in the open state, can switch the suction flow passage to the closed state in response to the user's push manipulation.

Accordingly, when the user separates the cap 100 and then pushes the internal body 330 in order to inject the liquid medicine into the body, the injection flow passage consists of the cylinder 20→the hub 12 of the injection needle 10→the needle body 11 of the injection needle 10, as shown in FIG. 9.

Even at this time, the opening/closing means 400 is fixedly installed within the cap 100 to allow the opening/closing means 400 to be separated together with the cap in response to the separation of the cap 100, thereby causing the injection needle 10 to be opened.

Accordingly, upon suction of the liquid medicine, the liquid medicine is sucked from the cap 100 into the cylinder through the valve means 300 which is in the open state, whereas upon injection of the liquid medicine, the liquid medicine is injected from the cylinder 20 through the opened injection needle 10.

As a result, it is possible to quickly suck and then rapidly discharge the liquid medicine, as required.

(4) Fourth Embodiment: Example in which for the Open Type Suction Flow Passage, the Valve Means 300 Closes the Suction Flow Passage by a User's Rotation Manipulation In the fourth embodiment of the present invention, as illustrated in FIG. 11, the internal body 330 and the external body 340 are configured to maintain the closed state of the suction flow passage by means of engagement of threads 332 and 342 formed in the internal body 330 and the internal body 340, respectively, in response to a rotation in one direction, and the suction flow passage is switchable to the open state again in response to a rotation in an opposite direction.

In the fourth embodiment, descriptions of configurations which are common to those of the third embodiment will be omitted, and only configurations different from those of the third embodiment will be described below.

As a result, when the external body 340 is positioned to be spaced apart from the through-holes 200 of the internal body 330, the suction flow passage is maintained in the open state as shown in FIG. 11 (a).

However, when the user separates the cap 100 and then rotates the internal body 330, the external body 340 closes the through-holes 200 formed in the internal body 330, thereby switching the suction flow passage to the closed state as shown in FIG. 11 (b).

As a result, the valve means 300, which initially maintains the suction flow passage in the open state as shown in FIG. 11 (a), can switch the suction flow passage to the closed state in response to the user's rotation manipulation.

Accordingly, when the user separates the cap 100 and then rotates the internal body 330 with respect to the external body 340 in order to inject the liquid medicine into the body, the injection flow passage consists of the cylinder 20→the hub 12 of the injection needle 10→the needle body 11 of the injection needle 10.

Even at this time, the opening/closing means 400 is fixedly installed within the cap 100 to allow the opening/closing means 400 to be separated together with the cap in response to the separation of the cap 100, thereby causing the injection needle 10 to be opened.

Accordingly, upon suction of the liquid medicine, the liquid medicine is sucked from the cap 100 into the cylinder through the valve means 300 which is in the open state, whereas upon injection of the liquid medicine, the liquid medicine is injected from the cylinder 20 through the opened injection needle 10.

As a result, it is possible to quickly suck and then rapidly discharge the liquid medicine, as required.

As compared with the third embodiment, the fourth embodiment has an advantage in that the valve means 300 may be closed and re-opened depending on a rotation direction.

Although the configuration in which the valve means 300 is positioned within the hub 12 has been described above, the valve means 300 may be positioned in a separate connector used for connecting the injection needle 10 to the cylinder 20 or within the cylinder 20.

Although the through-holes 200 have been illustrated as being formed in the hub 12 of the injection needle 10 and the hub 12 has been described as being divided into the internal body 330 and the external body 340, it is also possible to form the through-holes in a separate connector (not shown) or to form an internal body and an external body.

In other words, the positions of the through-holes 200 and the valve means 300 are not limited in the present invention.

In this case, an additional structure for forming a flow passage may be added between the cap 100 and the cylinder 20.

For example, a branch tube may be formed integrally with each of the cap hub 120 and the cylinder 20 and the branch tubes of them may be then connected by a flexible tube made of a flexible material to each other. In addition, the branch tubes may be configured to be at certain angles and may also have a well-known configuration enabling selective connection or disconnection of the branch tubes.

In the configuration for disconnecting the tubes from each other, there would no leakage of the liquid medicine only if a state where the valve means 300 is connected to the cylinder 20 should be maintained.

This connector may be formed integrally with the cap hub 120 or the cylinder 20, the valve means 300 may be embedded in the connector, and there will be no limitation on modification thereof.

Additionally, in the present invention, the cap 100 accommodates the opening/closing means 400 to form a part of the suction flow passage with a space between an outer periphery of the opening/closing means 400 and an inner periphery of the cap 100; the adhesive material 13 for fixing the needle body 11 and the hub 12 of the injection needle 10 to each other is accommodated in the opening/closing means 400 and thus isolated from the liquid medicine; and it is preferable that a filter 500 for filtering foreign substances from the liquid medicine is further provided in the suction flow passage.

That is, it is also possible to add the filter 500 for filtering foreign substances contained in the liquid medicine to the flange 420 of the opening/closing means 400 as shown in FIG. 12.

Since this filter 500 is not applied to the injection flow passage but is applied only to the suction flow passage, this filter will be discarded together with the opening/closing means 400 after it filters foreign substances such as fragments of an ampoule contained in the liquid medicine upon suction of the liquid medicine, so that the foreign substances filtered by the filter 500 are not injected again.

In addition thereto, as shown in FIG. 12, it is preferable in the present invention that the opening/closing means 400 is interference-fitted into the hub 12 or fastened to the hub 12 by threads 412.

This is to prevent the opening/closing means 400 from being unexpectedly separated from the hub 12, for example, when a saline solution is sucked into the syringe and then injected into a liquid medicine container, which accommodates a powdered medicine, to dissolve the powdered medicine and a resulting mixture is sucked back into the syringe, as described above.

In addition thereto, it is desirable that an inclined surface 411 is formed on an inner peripheral surface of the opening/closing means 400, as illustrated in FIG. 12, to guide entrance of the injection needle 10, whereby the inclined surface 411 guides a tip of the injection needle 10 when the opening/closing means 400 is fitted over the injection needle 10.

Therefore, the syringe of the present invention has great advantages in that by additionally forming the suction flow passage including the cap 100 so as not to pass through the injection needle 10 and by adding the opening/closing means 400 configured to temporarily close the injection needle 10, the suction of the liquid medicine is not limited to passage of the injection needle 10 as in an conventional syringe, so that the suction of the liquid medicine can be smoothly performed with a smaller force.

Furthermore, since the valve means 300 formed in the middle of the suction flow passage can be easily and forcibly closed by the user's push or rotation manipulation, it is possible to prevent any possible leakage of the liquid medicine which may occur upon injection of the liquid medicine.

The aforementioned embodiments are merely examples for specifically explaining the spirit of the present invention, and the scope of the present invention is not limited to the figures and embodiments.

[Explanation of Reference Numerals]

| | |
|---|---|
| 10: Injection needle | 11: Needle body |
| 12: Hub | 13: Adhesive material |
| 20: Cylinder | 30: Plunger |
| 100: Cap | 110: Suction needle |
| 120: Cap hub | 200: Through-hole |
| 300: Valve means | 310: Pin |
| 311: Through-hole | 320: Rotary pin |
| 321: Through-hole | 322: Rotary lever |
| 330: Internal body | 340: External body |
| 331, 341: Unidirectionally inclined protrusions | |
| 332, 342: Threads | 343: Shoulder |
| 400: Opening/closing means | 410: Hermetic space |
| 411: Inclined surface | 412: Thread |
| 420: Flange | 500: Filter |

The invention claimed is:

1. A syringe comprising a cylinder and an injection needle having a needle body and a hub, the syringe being formed with an injection flow passage extending from the cylinder to the injection needle and comprising:
an opening/closing means for selectively opening or closing the injection flow passage;
a suction flow passage formed from a suction needle of a pointed hollow cap to the cylinder and provided with a through-hole formed in any one of a connector for connecting the injection needle to the cylinder, and the cylinder to establish communication between an inside and an outside thereof, wherein the suction flow passage is separated from the injection flow passage such that liquid medicine is sucked into the cylinder through the suction needle without passing through the injection needle, wherein the injection needle is closed by the opening/closing means upon suction of the liquid medicine through the suction flow passage; and
a valve means for controlling opening or closing of the suction flow passage by a user's manipulation,
wherein the valve means comprises a rotary pin formed with a through-hole and positioned to traverse the suction flow passage, so that the valve means may maintain an open state of the suction flow passage when the through-hole of the rotary pin is correspondingly aligned with the suction flow passage, and may switch the suction flow passage to a closed state when a rotary lever formed at an outwardly protruding end of the rotary pin is rotated such that the through-hole of the rotary pin is offset from the suction flow passage by a direction difference.

2. The syringe of claim 1, wherein:
the pointed hollow cap comprises the suction needle and a cap hub which are formed to accommodate the opening/closing means such that the pointed hollow cap is formed with a part of the suction flow passage within a space between an outer periphery of the opening/closing means and an inner periphery of the pointed hollow cap;
an adhesive material for fixing the needle body and the hub of the injection needle to each other is accommodated in the opening/closing means and thus isolated from the liquid medicine; and
a filter for filtering foreign substances from the liquid medicine is further provided in the suction flow passage.

3. The syringe of claim 2, wherein the opening/closing means is interference-fitted into the hub of the injection needle or fastened to the hub of the injection needle by threads.

4. The syringe of claim 2, wherein the opening/closing means has an inclined surface formed on an inner peripheral surface thereof to guide entrance of the injection needle.

5. A syringe comprising a cylinder and an injection needle having a needle body and a hub, the syringe being formed with an injection flow passage extending from the cylinder to the injection needle and comprising:
an opening/closing means for selectively opening or closing the injection flow passage;
a suction flow passage formed from a suction needle of a pointed hollow cap to the cylinder and provided with a through-hole formed in any one of a connector for connecting the injection needle to the cylinder, and the cylinder to establish communication between an inside and an outside thereof, wherein the suction flow passage is separated from the injection flow passage such that liquid medicine is sucked into the cylinder through the suction needle without passing through the injection needle, wherein the injection needle is closed by the opening/closing means upon suction of the liquid medicine through the suction flow passage; and
a valve means for controlling opening or closing of the suction flow passage by a user's manipulation,
wherein the valve means comprises a hollow internal body formed with a through-hole and a pipe-shaped external body having an inner diameter corresponding to an outer diameter of the internal body, so that the valve means may maintain an open state of the suction flow passage in a state where the external body is spaced apart from the through-hole of the internal body, and may switch the suction flow passage to a closed state by causing an inner peripheral surface of the external body to close the through-hole formed in the internal body in response to a relative axial movement of the internal body and the external body,
wherein the internal body and the external body are configured to maintain the closed state of the suction flow passage by means of engagement of threads formed in the internal body and the external body in response to a rotation of the internal body in one direction, and to switch the suction flow passage to the open state in response to a rotation of the internal body in an opposite direction.

6. The syringe of claim 5, wherein:
the pointed hollow cap comprises the suction needle and a cap hub which are formed to accommodate the opening/closing means such that the pointed hollow cap is formed with a part of the suction flow passage within a space between an outer periphery of the opening/closing means and an inner periphery of the pointed hollow cap;
an adhesive material for fixing the needle body and the hub of the injection needle to each other is accommodated in the opening/closing means and thus isolated from the liquid medicine; and
a filter for filtering foreign substances from the liquid medicine is further provided in the suction flow passage.

7. The syringe of claim 6, wherein the opening/closing means is interference-fitted into the hub of the injection needle or fastened to the hub gf the injection needle by threads.

8. The syringe of claim 6, wherein the opening/closing means has an inclined surface formed on an inner peripheral surface thereof to guide entrance of the injection needle.

* * * * *